United States Patent

Satoh et al.

[11] Patent Number: 5,416,242
[45] Date of Patent: May 16, 1995

[54] HYDROQUINONE DERIVATIVE

[75] Inventors: Toshio Satoh; Hitoshi Matsumoto; Yasunori Niiro, all of Tokushima, Japan

[73] Assignee: Nippon Hypox Laboratories Incorporated, Tokyo, Japan

[21] Appl. No.: 283,713

[22] Filed: Aug. 1, 1994

Related U.S. Application Data

[63] Continuation of Ser. No. 951,130, Sep. 25, 1992, abandoned.

[51] Int. Cl.⁶ .................................. C07C 43/205
[52] U.S. Cl. ............................ 568/650; 568/651; 568/652
[58] Field of Search ............... 568/560, 561, 562

[56] References Cited

U.S. PATENT DOCUMENTS 2,459,540 10/1949 Rosenwald ................. 568/650
4,933,504 6/1990 Correale et al. ............. 568/650

FOREIGN PATENT DOCUMENTS 39484 11/1981 European Pat. Off. ....... 568/650
3207937 5/1983 Germany .................... 568/650
0287482 2/1991 Germany .................... 568/650
3196534 8/1988 Japan ....................... 568/650
1557237 12/1979 United Kingdom ............. 568/650

Primary Examiner—Howard T. Mars
Assistant Examiner—John Peabody
Attorney, Agent, or Firm—Nixon & Vanderhye

[57] ABSTRACT

Novel hydroquinone derivatives of the formulae (I) and (II),

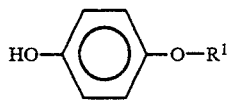
(I)

wherein $R^1$ is an alkyl group having 7 to 11 carbon atoms,

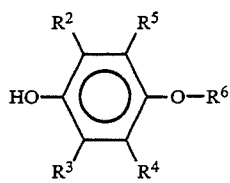
(II)

wherein each of $R^2$ to $R^5$ is independently a hydrogen atom, a lower alkyl group or a lower alkoxy group provided that at least one of $R^2$ to $R^5$ is a lower alkyl group or a lower alkoxy group, and $R^6$ is an alkyl group having a carbon chain of at least 2 carbon atoms. as compounds having antioxidant activity and tumor incidence inhibiting activity, and an antioxidant and a tumor incidence inhibitor containing, as an active ingredient, a hydroquinone derivative of the formula (III),

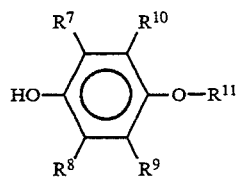
(III)

wherein each of $R^7$ to $R^{10}$ is independently a hydrogen atom, a lower alkyl group or a lower alkoxy group, and $R^{11}$ is an alkyl group having a carbon chain of at least 2 carbon atoms, and/or a salt thereof.

2 Claims, 1 Drawing Sheet

HYDROQUINONE DERIVATIVE

This is a continuation of application Ser. No. 07/951,130, filed Sep. 25, 1992, now abandoned.

FIELD OF THE INVENTION

The present invention relates to a novel hydroquinone derivative, and an antioxidant and a tumor inhibitor each containing this hydroquinone derivative as an active ingredient.

BACKGROUND OF THE INVENTION

Foods, feeds and cosmetics contain antioxidants (oxidation preventers) as required in order to prevent color Fading or discoloration, a change in the aroma and formation of peroxide during the preservation.

Examples of the antioxidants for the above use include the following.

(1) For foods and feeds

Butylhydroxytoluene (hereinafter referred to as BHT), dl-α-tocopherol, nordihydroguaiaretic acid, butylhydroxyanisole (hereinafter referred to as BHA) and propyl gallate.

(2) For cosmetics

BHT, dl-α-tocopherol, BHA and gallic acid.

Being excellent in antioxidant activity and less expensive, BHT is particularly preferentially used as a fat-soluble antioxidant for foods and as a fat-soluble antioxidant for cosmetics.

Meanwhile, with recent eating habits diversified, not only a variety of biological sources are put on the market, but also a variety of processed foods having new ingredients are being developed. With an aesthetical sense uplifted in the field of cosmetics in recent years, a variety of cosmetics having new ingredients are as well being developed.

An immunological study has revealed that the occurrence of human cancer is closely related to a daily life, particularly to eating habits and smoking. In recent years, it has been found that mutagens are developed by heating foods, and that most of these mutagens are nitrogen-containing aromatic heterocyclic compounds having an amino group (heterocyclic amine) (Sugiura T, et al., Perspectives on the Relative Risks, p.31, Mercell Dekker Inc, New York, 1989).

Above all, it has been revealed that 2-amino-6-methyldipyrido[1,2-a:3',2'-d]imidazole (Glu-P-1) formed by heating L-glutamic acid not only exhibits high mutagenic activity to Salmonellae but also exhibits carcinogenic activity to laboratory animals. An experiment with rats has shown that Glu-P-1 has a high rate of incidence of cancer particularly on the liver, large intestine, small intestine and gland of external acoustic meatus (Tkayamz S, et al., Gann, 75, 207, 1984).

It is therefore considered that the risk of carcinogenesis on humans can be avoided or decreased if the mutagenic activity and carcinogenic activity of heterocyclic amine can be inhibited. In particular, the transition of chronic hepatitis and cirrhosis to cancer of the liver is highly liable to occur, and it is a large clinical problem. Not an anti-cancer drug which directly attacks cancer cells, but a compound having a tumor inhibiting activity is considered to work effectively on patients having such diseases.

SUMMARY OF THE INVENTION

It is a first object of the present invention to provide a novel hydroquinone derivative having antioxidant activity.

It is a second object of the present invention to provide a novel antioxidant.

It is a third object of the present invention to provide a novel tumor inhibitor.

The above first object of the present invention is achieved by a novel hydroquinone derivative of the formula (I) (hereinafter referred to as "hydroquinone derivative A").

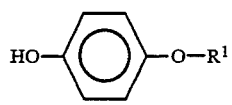

(I)

wherein $R^1$ is an alkyl group having 7 to 11 carbon atoms.

The above first object of the present invention is also achieved by a novel hydroquinone derivative of the formula (II) (hereinafter referred to as "hydroquinone derivative B").

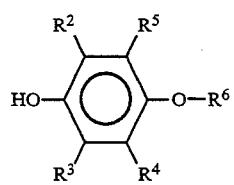

(II)

wherein each of $R^2$ to $R^5$ is independently a hydrogen atom, a lower alkyl group or a lower alkoxy group provided that at least one of $R^2$ to $R^5$ is a lower alkyl group or a lower alkoxy group, and $R^6$ is an alkyl group having a carbon chain of at least 2 carbon atoms.

The above second object of the present invention is achieved by an antioxidant containing, as an active ingredient, a hydroquinone derivative of the formula (III),

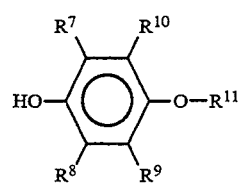

(III)

wherein each of $R^7$ to $R^{10}$ is independently a hydrogen atom, a lower alkyl group or a lower alkoxy group, and $R^{11}$ is an alkyl group having a carbon chain of at least 2 carbon atoms, and/or a salt thereof.

The above third object of the present invention is achieved by a tumor inhibitor containing, as an active ingredient, a hydroquinone derivative of the formula (III),

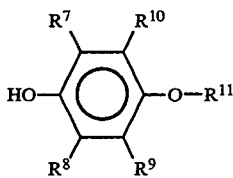

(III)

wherein each of $R^7$ to $R^{10}$ is independently a hydrogen atom, a lower alkyl group or a lower alkoxy group, and $R^{11}$ is an alkyl group having a carbon chain of at least 2 carbon atoms, and/or a salt thereof.

DETAILED DESCRIPTION OF THE INVENTION

Figure 1:
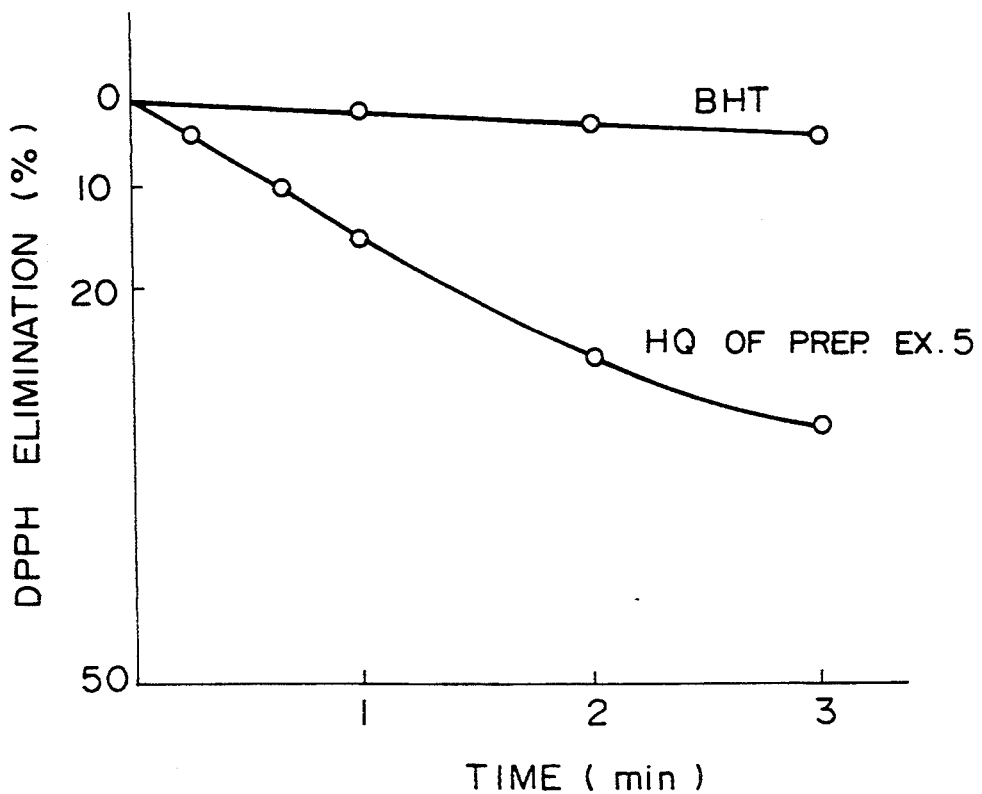
FIG. 1 is a graph showing test results on DPPH elimination ability.

First, the hydroquinone derivative A of the present invention will be explained below.

The hydroquinone derivative A is a compound having the formula (I) as described above. In the formula (I), $R^1$ is limited to an alkyl group having 7 to 11 carbon atoms. This alkyl group includes n-heptyl, n-octyl, n-nonyl, n-decyl and n-undecyl.

The above hydroquinone derivative A can be obtained by reacting hydroquinone with an alcohol of the following formula,

$R^1$—OH wherein $R^1$ is the same as $R^1$ defined in the formula (I), in the presence of a heteropoly-acid such as phosphomolybdic acid, phosphotungstic acid, silicomolybdic acid or silicotungstic acid.

The hydroquinone derivative A obtained as above has antioxidant activity sufficient to be utilized as an antioxidant.

The hydroquinone derivative B of the present invention will be explained hereinafter.

The hydroquinone derivative B is a compound having the formula (II) as described above. In the formula (II), each of $R^2$ to $R^5$ is independently a hydrogen atom, a lower alkyl group or a lower alkoxy group, provided that at least one of $R^2$ to $R^5$ is a lower alkyl group or a lower alkoxy group, and $R^6$ is an alkyl group having a carbon chain of at least 2 carbon atoms. The lower alkyl group as $R^2$ to $R^5$ includes methyl, ethyl, propyl and butyl. The lower alkoxy group as $R^2$ to $R^5$ includes methoxy, ethoxy, propoxy and butoxy. The alkyl group having a carbon chain of at least 2 carbon atoms as $R^6$ includes ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the formula (II) for the hydroquinone derivative B, $R^6$ is limited to an alkyl group having a carbon chain of at least 2 carbon atoms for the following reason. A hydroquinone derivative of the formula (II) wherein $R^6$ is an alkyl group having 1 carbon atom (methyl) shows low antioxidant activity. With an increase in the number of carbon atoms in the alkyl group as $R^6$, the antioxidant activity increases. The increase in the antioxidant activity with an increase in the number of carbon atoms reaches its peak while the number of carbon atoms is 4 to 8, and the antioxidant activity gradually decreases thereafter.

The hydroquinone derivative B of the formula (II) can be obtained, for example, from a known hydroquinone derivative of the formula (IV) as a starting material,

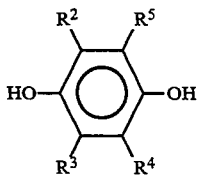

(IV)

wherein $R^2$ to $R^5$ are as defined in the formula (II), by the following method (a) or (b).

(a) When it is intended to obtain, for example, a hydroquinone derivative (B) wherein one hydroxyl group which is under less steric hindrance than the other hydroxyl group is etherified as shown in the hydroquinone derivative of the following formula,

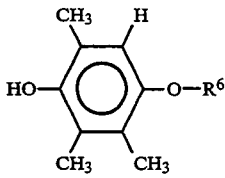

the hydroquinone derivative of the formula (IV) is allowed to react with an alcohol of the formula,

$R^6$—OH wherein $R^6$ is the same as $R^6$ in the formula (II), in the presence of a heteropoly-acid such as phosphomolybdic acid, phosphotungstic acid, silicomolybdic acid or silicotungstic acid.

(b) When it is intended to obtain, for example, a hydroquinone derivative (B) wherein one hydroxyl group which is under more steric hindrance than the other hydroxyl group is etherified as shown in the hydroquinone derivative of the following formula,

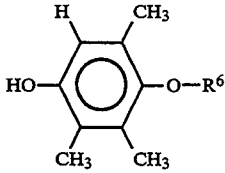

the hydroquinone derivative of the formula (IV) is blocked by esterifying its hydroxyl group which is under less steric hindrance with acid halide such as pivaloyl chloride, then the other hydroxyl group which is to be etherified and is under more steric hindrance is etherified with an halogenated alkyl of the following formula,

$R^6$—X wherein $R^6$ is the same as $R^6$ in the formula (II), and X is a halogen atom, and the hydroxyl group which is under less steric hindrance is converted back to a free hydroxyl group by removing the blocking on it by an ester hydrolysis reaction. As methyl is a larger group than hydrogen, the hydroxyl group between the two methyl groups is under more steric hindrance than the opposite hydroxyl group between hydrogen and methyl.

The hydroquinone derivative B obtained by any one of the above methods has antioxidant activity sufficient to be utilized as an antioxidant like the foregoing hydroquinone derivative A.

The antioxidant of the present invention will be explained hereinafter.

The antioxidant contains the hydroquinone derivative of the formula (III) and/or a salt thereof as an active ingredient as described previously. In the formula (III), each of $R^7$ to $R^{10}$ is independently a hydrogen atom, a lower alkyl group or a lower alkoxy group, and $R^{11}$ is an alkyl group having a carbon chain of at least 2 carbon atoms.

As is clear in the formula (III), the antioxidant of the present invention includes the hydroquinone derivative A and the hydroquinone derivative B. Further, the antioxidant of the present invention also includes known hydroquinone derivatives which have been found for the first time to have excellent antioxidant activity by the study of the present inventors, such as 1-butylhydroquinone, 1-hexylhydroquinone and 1-dodecylhydroquinone.

The antioxidant of the present invention may contain conventional carriers such as starch, crystalline cellulose, acacia (Arabic gum), lactose, sucrose, glucose, glycerol, propylene glycol, ethanol, etc.

The antioxidant of the present invention is useful as an antioxidant for use in foods, feeds and cosmetics due to its excellent antioxidant activity and low toxicity. Further, the antioxidant of the present invention can be also used as an active ingredient for drugs for the prevention and therapy of functional disorder of organs, since it can eliminate tissue disorder-inducing factors such as active oxygen species and active organic radical species.

The tumor inhibitor of the present invention will be explained hereinafter.

The tumor inhibitor of the present invention has the activity to inhibit the mutagenic activity and carcinogenic activity of heterocyclic amine. Further, this tumor inhibitor exhibits no activity to destroy normal cells, and its toxicity test data has shown its high safety.

The tumor inhibitor contains the hydroquinone derivative of the formula (III) and/or a salt thereof as an active ingredient as described previously. In the formula (III), each of $R^7$ to $R^{10}$ is independently a hydrogen atom, a lower alkyl group or a lower alkoxy group, and $R^{11}$ is an alkyl group having a carbon chain of at least 2 carbon atoms.

As is clear in the formula (III), the tumor inhibitor of the present invention includes the hydroquinone derivative A and the hydroquinone derivative B. Further, tumor inhibitor of the present invention also includes known hydroquinone derivatives which have been found fop the first time to have excellent tumor inhibiting activity by the study of the present inventors, such as 1-butylhydroquinone, 1-hexylhydroquinone and 1-dodecylhydroquinone.

The tumor inhibitor of the present invention may contain conventional carriers such as starch, crystalline cellulose, acacia (Arabic gum), lactose, sucrose, glucose, glycerol, propylene glycol, ethanol, etc.

EXAMPLES

The present invention will be explained hereinafter by reference to Examples.

PREPARATION EXAMPLE 1

[Preparation of 1-octylhydroquinone,

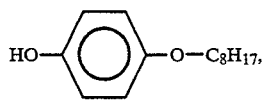

(one of hydroquinone derivatives A)]

0.7 Gram of phosphomolybdic acid ($P_2O_5.24MoO_3.xH_2O$) was added to a solution of 2.2 g (20 mmol) of hydroquinone in 40 ml of n-octyl alcohol. The resultant mixture was stirred, and then heated at 120° C. for 6 hours. After the heating, 300 ml of each of water and ethyl acetate (EtOAc) was added to the mixture, and the mixture was shaken.

Then, an organic layer was, recovered, dried over anhydrous $MgSO_4$ and concentrated tinder reduced pressure. The resultant residue was subjected to silica gel chromatography for elution with a mixed solution of hexane and EtOAc to give a crude product of 1-octylhydroquinone.

The above-obtained crude product was recrystallized from n-hexane to give 2.7 g of the intended, captioned compound (yield 60 %).

Table 1 shows the yield amount, yield, melting point and δ value in hydrogen nuclear magnetic resonance (H-NMR) with regard to the above-obtained 1-octylhydroquinone.

PREPARATION EXAMPLE 2

[Preparation of 1-decylhydroquinone,

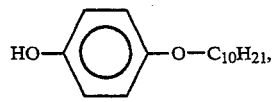

(one of hydroquinone derivatives A)]

Preparation Example 1 was repeated except that the n-octyl alcohol was replaced with n-decyl alcohol to give 3.7 g of the intended, captioned compound (yield 49 %).

Table 1 shows the yield amount, yield, melting point and δ value in H-NMR with regard to the above-obtained 1-decylhydroquinone.

PREPARATION EXAMPLE 3

[Preparation of 1-butyl-2,3,5-trimethylhydroquinone,

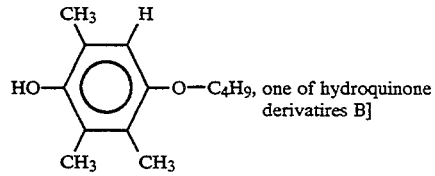

Preparation Example 1 was repeated except that the hydroquinone was replaced with 2,3,5-trimethylhydroquinone and that the n-octyl alcohol was replaced with n-butyl alcohol to give 3.19 g of the intended, captioned compound (yield 73 %).

Table 1 shows the yield amount, yield, melting point and δ value in H-NMR with regard to the above-obtained 1-butyl-2,3,5-trimethylhydroquinone.

PREPARATION EXAMPLES 4–7

[Preparation of hydroquinone derivatives B]

Preparation Example 1 was repeated except that the n-octyl alcohol was replaced with an alcohol of the formula, $R^6$—OH in which $R^6$ was as shown in Table 1, to give a hydroquinone derivative of the general formula II in which each of $R^2$, $R^3$ and $R^4$ was methyl, $R^5$ was hydrogen and $R^6$ was an alkyl shown in Table 1.

Table 1 shows the yield amount, yield, melting point and δ value in H-NMR with regard to each of the so-obtained hydroquinone derivatives B.

PREPARATION EXAMPLE 8

[Preparation of 4-hexyl-2,3,5-trimethylhydroquinone,

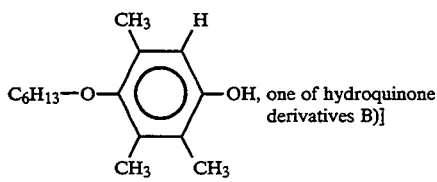

OH, one of hydroquinone derivatives B)]

(1) Preparation of 1-pivaloyl-2,3,5-trimethyl-hydroquinone

6 Milliliters of anhydrous pyridine was mixed with a solution of 3.5 g (23.0 mmol) of 2,3,5-trimethylhydroquinone in 20 ml of methyl chloride. The resultant mixture was cooled to −15° C., and 20 ml of methylene chloride containing 2.8 g of pivaloyl chloride was added dropwise to the mixture over 20 minutes. Then, the temperature of the mixture was brought back to room temperature, and the mixture was stirred for 8 hours. After the stirring, 4.25 ml of acetic acid and 20 ml of water were added to the reaction mixture, and the mixture was shaken.

After the shaking, an organic layer was recovered, dried over anhydrous MgSO₄, and then concentrated under reduced pressure. The resultant residue was subjected to silica gel column chromatography for elution with a mixed solvent of benzene and EtOAc to give 2.4 g of a crude product of 1-pivaloyl-2,3,5-trimethylhydroquinone.

(2) Preparation of 4-hexyl-1-pivaloyl-2,3,5-trimethylhydroquinone 2.4 Grams (10.0 mmol) of the crude product of 1-pivaloyl-2,3,5-trimethylhydroquinone obtained in the above (1), 21.2 g (100.0 mmol) of hexyl iodide and 6.9 g (20.0 mmol) of potassium carbonate were added to 70 ml of methyl ethyl ketone, and the resultant mixture was stirred and then refluxed for 8 hours. After the refluxing, 150 ml of water and 150 ml of EtOAc were added to the reaction mixture, and after the mixture was shaken, an organic layer was recovered. Then, 150 ml of EtOAc was added to the remaining water layer, and after the resultant mixture was shaken, an organic layer was recovered. Further, this procedure was repeated once again.

The recovered organic layers above were all mixed together, and the mixture was washed with water, dried over anhydrous MgSO₄ and concentrated under reduced pressure. The resultant residue was subjected to silica gel column chromatography for elution with a mixed solvent of hexane and EtOAc to give 1.5 g of a crude product of 4-hexyl-1-pivaloyl-2,3,5-trimethylhydroquinone.

(3) Preparation of 4-hexyl-2,3,5-trimethylhydroquinone (captioned compound)

1.5 Grams (4.0 mmol) of the 4-hexyl-1-pivaloyl-2,3,5-trimethylhydroquinone and 0.45 g of potassium hydroxide were added to 5 ml of (MeOH), and the resultant mixture was stirred at room temperature for 6 hours. After the stirring, 150 ml of water and 150 ml of EtOAc were added to the reaction mixture, and after the mixture was shaken, an organic layer was recovered. Then, 150 ml of EtOAc was added to the remaining water layer, and after the resultant mixture was shaken, an organic layer was recovered. Further, this procedure was repeated once again.

The recovered organic layers were all mixed together, and the mixture was washed with water, dried over anhydrous MgSO₄ and concentrated under reduced pressure. The resultant residue was subjected to silica gel column chromatography for elution with a mixed solvent of hexane and EtOAc to give a crude product of 4-hexyl-2,3,5-trimethylhydroquinone. This crude product was recrystallized from n-hexane to give 0.7 g of the intended, captioned compound (yield 65 %).

Table 1 shows the yield amount, yield, melting point and δ value in H-NMR with regard to the above-obtained 4-hexyl-2,3,5-trimethylhydroquinone.

PREPARATION EXAMPLES 9–11

[Preparation of known hydroquinone derivatives]

Preparation Example 1 was repeated except that the n-octyl alcohol was replaced with an alcohol of the formula, $R^1$—OH in which $R^1$ was as shown in Table 1 to give a known hydroquinone derivative in which $R^1$ was as shown in Table 1.

Table 1 shows the yield amount, yield, melting point and δ value in H-NMR with regard to each of the so-obtained, known hydroquinone derivatives.

PREPARATION EXAMPLE 12

[Preparation of 1-ethyl-2,3,5-trimethylhydroquinone

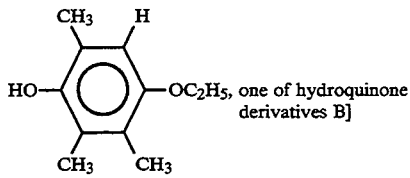

OC₂H₅, one of hydroquinone derivatives B]

Preparation Example 3 was repeated except that n-octyl alcohol was replaced by ethyl alcohol to obtain the intended captioned compound (yield 73 %).

Table 1 shows the melting point and δ value in H-NMR of the obtained 1-ethyl-2,3,5-trimethylhydroquinone.

TABLE 1

| | Formula | $R^1$ or $R^6$ | Yield (percentage) | Melting point (°C.) | δ-Value in H-NMR [CDCl3] |
|---|---|---|---|---|---|
| Example 1 | HO—⟨⟩—O—$R^1$ | —$C_8H_{17}$ | 2.6 (60%) | 58.5–59 | 0.88(3H, t, J=6.2Hz), 1.31–1.96(12H, m) 3.89(2H, t, J=6.4Hz), 6.76(4H, s) |
| Example 2 | | —$C_{10}H_{21}$ | 3.7 (49%) | 68.5–69 | 0.88(3H, t, J=5.7Hz), 1.02–1.75(16H, m) 3.89(2H, t, J=6.2Hz), 6.76(4H, s) |
| Example 3 | $R^2$ $R^5$ <br> HO—⟨⟩—O—$R^6$ <br> $R^3$ $R^4$ | —$C_4H_9$ | 3.19 (73%) | 65.5–66.5 | 0.97(3H, t, J=6.5Hz), 2.14(3H, s) 1.30–1.90(4H, m), 2.17(3H, s), 2.21(3H, s) 3.87(2H, t, J=5.9Hz), 6.51(H, s) |
| Example 4 | | —$C_6H_{13}$ | 3.17 (64%) | 72.5–73 | 0.97(3H, t, J=6.6Hz), 1.30–1.90(8H, m) 2.14(3H, s), 2.17(3H, s), 2.21(3H, s) 3.87(2H, t, J=6.2Hz), 6.58(H, s) |
| Example 5 | | —$C_8H_{17}$ | 2.99 (54%) | 70–71 | 0.89(3H, t, J=6.2Hz), 1.10–1.76(12H, m) 2.14(3H, s), 2.17(3H, s), 2.21(3H, s) 3.86(2H, t, J=6.2Hz), 6.52(H, s) |
| Example 6 | ($R^2$=$R^3$=$R^4$=$CH_3$, $R^5$=H) | —$C_{10}H_{21}$ | 2.57 (42%) | 76–77 | 0.88(3H, t, J=5.1Hz), 1.05–1.94(16H, m) 2.14(3H, s), 2.17(3H, s), 2.21(3H, s) 3.86(2H, t, J=6.4Hz), 6.51(H, s) |
| Example 7 | | —$C_{12}H_{25}$ | 3.62 (55%) | 81–83 | 0.88(3H, t, J=6.4Hz), 1.26–1.97(20H, m) 2.14(3H, s), 2.17(3H, s), 2.21(3H, s) 3.86(2H, t, J=6.2Hz), 6.51(H, s) |
| Example 8 | ($R^2$=$R^4$=$R^5$=$CH_3$, $R^3$=H) | —$C_6H_{13}$ | 0.7 (65%) | 32–34 | 0.95(3H, t, J=6Hz), 1.26–1.97(8H, m) 2.16(3H, s), 2.18(6H, s) 3.67(2H, t, J=6Hz), 6.45(H, s) |
| Example 9 | HO—⟨⟩—O—$R^1$ | —$C_4H_9$ | 2.2 (73%) | 63–64 | 0.96(3H, t, J=6.6Hz), 1.18–1.82(4H, m) 3.90(2H, t, J=6.4Hz), 6.77(4H, s) |
| Example 10 | | —$C_6H_{13}$ | 1.4 (70%) | 42.5–43 | 0.90(3H, t, J=6.0Hz, 1.33–1.92(8H, m) 3.89(2H, t, J=6.2Hz), 6.72(4H, s) |
| Example 11 | | —$C_{12}H_{25}$ | 9.9 (55%) | 77–78 | 0.88(3H, t, J=6.2Hz), 1.26–1.75(20H, m) 3.89(2H, t, J=6.4Hz), 6.76(4H, s) |
| Example 12 | HO—⟨⟩—$OC_2H_5$ | — | (70%) | 87–88 | 1.39(3H, t), 2.14(3H, s), 2.17(3H, s), 2.21(3H, s), 3.87(2H, q), 4.24(H, s), 6.58(H, s) |

ANTIOXIDANT ACTIVITY TEST EXAMPLE 1

[Inhibition activity against hyperoxidation of lipid of rat liver microsome]

(1) Preparation of rat liver microsome suspension,

A plurality of male Sprague Dawley (SD) rats (weighing 250 to 280 kg) were prepared. Each rat was anesthetized with pentobarbital, and then subjected to celiotomy. A cannula was introduced into the portal vein of each rat, the abdominal large veins were sectioned, and 500 ml of cold 0.9% NaCl was injected into the portal veins.

Livers were extracted from individual rats, and the livers were cut to pieces in 1.15% KCl and homogenized with ice cooling. Then, 1.15% KCl was further added to obtain a 30% liver homogenized solution.

The above homogenized solution was centrifugally separated at 8,000 g (g: gravitation acceleration) for 10 minutes, and the resultant supernatant was recovered. The supernatant was centrifugally separated at 105,000 g (g: gravitational acceleration) for 1 hour, and 1.15% KCl was added to the resultant residue such that the residue had a protein concentration of 10 mg/ml when measured for a protein amount by a Lowry method, thereby to obtain a liver microsome suspension.

The so-prepared suspension was stored at −20° C. before a test described in the following (2), and it was used within 1 week after the preparation.

(2) Test on inhibition activity against hyperoxidation of lipid

As test compounds, the hydroquinone (HQ) derivatives obtained in Preparation Examples 1 to 12, a known hydroquinone derivative which was a compound of the formula (I) in which $R^1$ was methyl (hereinafter referred to as HQ1) and BHT were respectively tested on their inhibition activities against hyperoxidation of lipid in the following manner.

First, 0.1 ml of the liver microsome suspension obtained in the above (1), 0.1 ml of reduced nicotinamide dinucleotide phosphate (NADPH) (final concentration 2 mM), 0.1 ml of adenosine 5'-diphosphate (ADP) (final concentration 10 mM) and 0.1 ml of a solution of one of the test compounds whose concentration was adjusted as shown in Table 2 with 10% dimethylformamide (DMF) were added to a tris-HCl buffer (167 mM KCl, 74 mM tris-HCE buffer (TRIS), pH 7.4), and the resultant mixture was warmed at 37° C. for 5 minutes. Then. 0.1 ml of FeCl3 (final concentration 0.1 mM) was added, and the mixture was warmed at 37° C. for 20 minutes.

The resultant reaction mixture was cooled with ice. Then, 0.2 ml of 8.1% sodium dodecylsulfate (SDS), 1.5 ml of an acetic acid buffer (prepared by adjusting 20% acetic acid containing 0.27 mM HCl to pH 3.5 with 10N NaOH) and 1.5 ml of 0.8% thiobarbituric acid were added to the cooled reaction mixture, and the resultant mixture was warmed over a boiling water bath for 20 minutes. After the warming, the reaction mixture was cooled with ice, and 4 ml of an normal butanol (n-BuOH)/pyridine mixed solution [n-BuOH:- pyridine=15:1 (volume ratio)] was added to the cooled reaction mixture. The mixture was vigorously stirred.

The reaction mixture was centrifugally separated at 2,000 rpm for 10 minutes, and the resultant supernatant was measured for an absorbance at 532 nm to determine a thiobarbituric acid reaction amount. And, on the basis of a calibration curve of mandeloaldehyde (MDA) amount prepared by using 1,1,3,3-tetramethoxypropane, a peroxidized lipid amount was determined as an amount of formed MDA.

In Control, the solution of the test compound in 10% DMF was replaced with 0.1 ml of a 10% DMF solution, and the above procedures were repeated to determine a peroxidized lipid amount. In Blank, each of 0.1 ml of NDAPH, 0.1 ml of ADP and 0.1 ml of FeCl$_3$ were replaced with 0.1 ml of water, the solution of the test compound in 10% DMF was replaced with 0.1 ml of a 10% DMF solution, and the above procedures were repeated to determine a peroxidized lipid amount.

The inhibition ratio of the lipid peroxidation reaction was calculated on the basis of the following equation.

Inhibition ratio
$$(\%) = [1-(OD_1-OD_3)/(OD_2-OD_3)] \times 100$$

OD$_1$: Absorbance when test compound is added.
OD$_2$: Absorbance of Control
OD$_3$: Absorbance of Blank
Table 2 shows the results.

TABLE 2

| Test compound*1 | Inhibition ratio of lipid peroxidation (%)*2 | |
|---|---|---|
| | $10^{-5}$M | $10^{-6}$M |
| HQ derivative A of Preparation Example 1 | 99.7 | 9.8 |
| HQ derivative A of Preparation Example 2 | 79.5 | 1.8 |
| HQ derivative B of Preparation Example 3 | —*3 | 75.9 |
| HQ derivative B of Preparation Example 4 | 100.0 | 98.9 |
| HQ derivative B of Preparation Example 5 | 100.0 | 74.8 |
| HQ derivative B of Preparation Example 6 | 99.9 | 38.3 |
| HQ derivative B of Preparation Example 7 | 63.9 | 30.8 |
| HQ derivative B of Preparation Example 8 | 98.3 | 40 |
| HQ derivative of Preparation Example 9 | 86.1 | 10.8 |
| HQ derivative of Preparation Example 10 | 99.1 | 8.8 |
| HQ derivative of Preparation Example 11 | 73.4 | 6.3 |
| HQ derivative of Preparation Example 12 | 87.2 | —*3 |
| BHT | 100.0 | 14.0 |
| HQ1 | 37.8 | —*3 |

*1: HQ stands for hydroquinone.
*2: Each of $10^{-5}$M and $10^{-6}$ indicates a concentration of test compound.
*3: Not tested.

Table 2 clearly shows that the hydroquinone derivatives A of the present invention, obtained in Preparation Examples 1 and 2, have excellent antioxidant activity over the known hydroquinone derivative HQ1 and are usable as an antioxidant. It has been found for the first time that the known hydroquinone derivatives obtained in Preparation Examples 9 to 11 have antioxidant activity usable as an antioxidant.

Further, the hydroquinone derivatives B of the present invention, obtained in Preparation Examples 3 to 8 and 12, show antioxidant activity equivalent to that of the hydroquinone derivatives A or to that of BHT, a conventional typical fat-soluble antioxidant, when used in a concentration of $10^{-5}$M, and these hydroquinone derivatives B also show excellent antioxidant activity over BHT when used in a low concentration as low as $10^{-6}$M.

ANTIOXIDANT ACTIVITY TEST EXAMPLE 2

[DPPH elimination ability]

The hydroquinone derivative obtained in Preparation Example 5 and BHT as test compounds were measured for the ability to eliminate DPPH ($\alpha,\alpha$-diphenyl-$\beta$-picrylhydrazyl) (active organic radical species elimination ability) in the following manner.

The test compounds were respectively dissolved in DMF to prepare DMF solutions having a test compound concentration of $10^{-2}$M.

Then, 0.02 ml each of the above DMF solutions were respectively added to 2 ml of an ethanol EtOH solution containing $10^{-4}$M of DPPH, and the resultant solutions were measured for absorbance (OD$_s$) at 517 nm at predetermined time intervals. The DPPH elimination ability of each test compound was determined on the basis of these measurement results. In Control, the DMF solution of the test compound was replaced with DMF itself, The elimination ability of each test compound was determined as a reduction ratio of OD$_s$ to the absorbance in Control.

FIG. 1 shows the results.

As is clear in FIG. 1, the hydroquinone derivative B obtained in Preparation Example 5 has excellent DPPH elimination ability over BHT.

Antinutagenic activity test on mutagenesis of heterocyclic amine to Salmonellae (Method)

Compounds of the present invention were tested on their antimutagenic activity to heterocyclic amines of Glu-P-1.HCl, 3-amino-1,4-dimethyl-5H-pyrido[4,3-b]-indole or (Trp-P-1) acetate and 2-amino-3-methylimidazo[4,5-f]quinoline or (IQ) by a preincubation method-applied Ames test according to the method of Diane et al (Diane F. Birt, et al., Carcinogenesis, Vol. 7, No. 6, 959-963, 1986).

That is, rat liver microsones contained in P-450 and P-448 mix (0.5 ml), 0.1 ml of a Salmonella TA 98 medium (a bacterial culture strain), a compound off the present invention dissolved in DMSO and 0.1 ml of one of the above mutagens were charged into a test tube, and cultured at 37° C. for 20 minutes with shaking, Then, 2 ml of soft agar was added to, and mixed with, the contents in the test tube. The resultant mixture was spread over a minimal glucose agar medium, and cultured at 37° C. for 48 hours, and the number of reverse mutation colonies. Two or three plates were prepared each dosage, and the test results were compared with the test result of a negative control group to which dimethyl sulfoxide (DMSO) alone was added and the test result of a positive control group to which the corresponding mutagen alone was added. Table 3 shows the results, in which it is seen that the compounds of the present invention had the activity to inhibit the mutagenesis of heterocyclic amine.

TABLE 3

| Mutagen | Test compound | | Mutagenesis inhibition ratio |
|---|---|---|---|
| Glu-P-1* | 0.02 µg | HQ derivative of Prep. Ex. 4 | 5.0 µg | 81 |
| | | | 10.0 µg | 92 |
| Trp-P-1.acetate** | 0.02 µg | HQ derivative of Prep. Ex. 4 | 5.0 µg | 61 |
| | | | 10.0 µg | 73 |
| IQ*** | 0.005 µg | HQ derivative of Prep. Ex. 4 | 5.0 µg | 89 |
| | | | 10.0 µg | 64 |

TABLE 3-continued

| Mutagen | Test compound | | | Mutagenesis inhibition ratio |
|---|---|---|---|---|
| IQ*** | 0.005 μg | HQ derivative of Prep. Ex. 3 | 20.0 μg | 85 |
| IQ*** | 0.005 μg | HQ derivative of Prep. Ex. 12 | 20.0 μg | 85 |

*Glu-P-1.HCl: 2-amino-6-methyldipyrido[1,2-a:3',2'-d]-imidazole hydrochlorate
**Trp-P-1.acetate: 3-amino-1,4-dimethyl-5H-pyrido[4,3-b]-indole acetate
***IQ: 2-amino-3-methylimidazo[4,5-f]quinoline Acute toxicity test
(Method)

Female ICR mice of 8 weeks age were used to carry out an acute toxicity test by simple oral administering. Compounds of the present invention (HQ derivatives of Preparation Examples 1 and 12) were respectively dissolved in an olive oil, and each of the resultant solutions was orally administered to three dosage groups each consisting of 6 mice such that the maximum dose was 500 mg/kg, followed by doses gradually decreased at a common ratio of 2. The mice were observed for 14 days after the administration.

(Result)

No mice were found to die during the entire period of the observation.

As explained above, the hydroquinone derivative A and hydroquinone derivative B of the present invention have antioxidant activity sufficient for use as an antioxidant. The antioxidant of the present invention contains, as an active ingredient, any one of these novel hydroquinone derivatives and/or any one of known hydroquinone derivatives which have been found for the first time to have excellent antioxidant activity.

Therefore, there can be provided novel antioxidants by working the present invention, and there can be provided a wider selection of antioxidants to meet with rapidly advancing diversification in foods and cosmetics in recent years.

The hydroquinone derivative A and hydroquinone derivative B of the present invention have tumor inhibiting activity. The tumor inhibitor of the present invention contains, as an active ingredient, any one of these novel hydroquinone derivatives and/or any one of known hydroquinone derivatives which have been found for the first time to have excellent tumor inhibiting activity.

Therefore, there can be provided novel tumor inhibitors by working the present invention.

What is claimed is:

1. A compound of the formula:

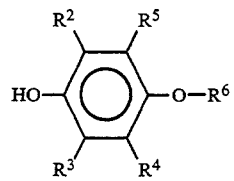
(II)

wherein $R^2$, $R^3$ and $R^4$ are independently a lower alkyl group or a lower alkoxy group, $R^5$ is hydrogen and $R^6$ is a $C_{4-8}$ alkyl group, or a salt thereof.

2. An antioxidant composition comprising together with a carrier an effective amount of a compound of the formula:

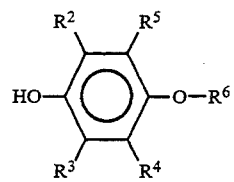
(II)

wherein $R^2$, $R^3$ and $R^4$ are independently a lower alkyl group or a lower alkoxy group, $R^5$ is hydrogen and $R^6$ is a $C_{4-8}$ alkyl group, or a salt thereof.

* * * * *